(12) United States Patent
Hahn et al.

(10) Patent No.: US 10,094,688 B2
(45) Date of Patent: Oct. 9, 2018

(54) CALIBRATION SYSTEM

(71) Applicant: Buerkert Werke GmbH, Ingelfingen (DE)

(72) Inventors: Thomas Hahn, Oehringen (DE); Vinoth Pathmanathan, Neuenstadt a. K. (DE); Florian Fischer, Ravenstein OT Ballenberg (DE)

(73) Assignee: Buerkert Werke GmbH, Ingelfingen (DE)

( * ) Notice: Subject to any disclaimer, the term of this patent is extended or adjusted under 35 U.S.C. 154(b) by 218 days.

(21) Appl. No.: 15/088,469

(22) Filed: Apr. 1, 2016

(65) Prior Publication Data
US 2016/0298988 A1 Oct. 13, 2016

(30) Foreign Application Priority Data

Apr. 10, 2015 (DE) .................... 20 2015 101 756 U

(51) Int. Cl.
*G01N 33/00* (2006.01)
*G01D 18/00* (2006.01)
(Continued)

(52) U.S. Cl.
CPC ............. *G01D 18/00* (2013.01); *G01N 33/18* (2013.01); *G01N 27/06* (2013.01); *G01N 27/26* (2013.01);
(Continued)

(58) Field of Classification Search
CPC ........ G01D 18/00; G01N 33/18; G01N 27/06; G01N 27/26; G01N 27/4167; G01N 33/182
(Continued)

(56) References Cited

U.S. PATENT DOCUMENTS

2010/0077829 A1* 4/2010 Batista .................. G01L 27/005
73/1.57
2010/0108870 A1* 5/2010 Kramer ..................... G01L 1/24
250/231.19

(Continued)

FOREIGN PATENT DOCUMENTS

DE  3819100 A1  12/1989
DE  10322277 A1  3/2005

OTHER PUBLICATIONS

German Search Report dated Dec. 15, 2015 from corresponding German Application No. 20 2015 101 756.1, 5 pages.

*Primary Examiner* — Helen Kwok
*Assistant Examiner* — Nashmiya Fayyaz
(74) *Attorney, Agent, or Firm* — Dilworth IP, LLC

(57) ABSTRACT

A calibration system has a calibration device which includes at least one calibration fluid receptacle, an electric and a fluidic interface for releasably connecting at least one sensor module to be calibrated, which is a unit constructionally separate from the calibration device and contains one or more sensors, and a controller which controls the flow of calibration fluid through the sensor module connected to the calibration device and which is electrically coupled with the connected sensor module via the electric interface and can collect measurement data from the sensor module. In the calibration system, in particular in the sensor module, calibration data are stored, so that the calibration device can calibrate various sensor modules which are coupled to the interface.

16 Claims, 3 Drawing Sheets

(51) Int. Cl.
    *G01N 33/18*      (2006.01)
    *G01N 27/06*      (2006.01)
    *G01N 27/26*      (2006.01)
    *G01N 27/416*     (2006.01)

(52) U.S. Cl.
    CPC ....... *G01N 27/4167* (2013.01); *G01N 33/182* (2013.01)

(58) Field of Classification Search
    USPC .................................................. 73/1.02–1.03
    See application file for complete search history.

(56) References Cited

U.S. PATENT DOCUMENTS

2013/0140179 A1      6/2013   Lin et al.
    2015/0020599 A1*     1/2015   Pechstedt .............. G01L 9/0079
                                                             73/705
    2015/0323511 A1*     11/2015  Hendry ................ A61B 5/1495
                                                             73/1.06

* cited by examiner

CALIBRATION SYSTEM

FIELD OF THE INVENTION

This invention relates to a calibration system for at least one sensor module.

BACKGROUND

To get exact measurement values in analysis devices, it is necessary to calibrate the sensors used to obtain the measurement values. A calibration is typically required at least once when a new sensor is inserted into a system, but can also be repeated at particular intervals, in order to maintain the measurement accuracy of the sensors.

The calibration of the sensors should be feasible as quickly and easily as possible and with sparing use of the necessary calibration fluids.

It is the object of the invention to create a calibration system which satisfies these requirements.

SUMMARY

The present invention provides a calibration system which comprises a calibration device which includes at least one calibration fluid receptacle and one electric and one fluidic interface for releasably connecting at least one sensor module to be calibrated. The sensor module is a unit constructionally separate from the calibration device and contains one or more sensors. The calibration device also includes a controller which controls the flow of calibration fluid through the sensor module connected to the calibration device and which via the electric interface is electrically coupled with the connected sensor module and can collect measurement data from the sensor module. In the calibration system, in particular in the sensor module, calibration data are stored, so that the calibration device can calibrate various sensor modules which can be coupled to the interface.

For calibrating a sensor, the sensor module containing this sensor is coupled with the calibration device via the electric and the fluidic interface and flushed with one or more calibration fluids. The measurement data collected by the one or more sensors with respect to the calibration fluids are collected and evaluated by the controller of the calibration device. The data obtained during the calibration advantageously are stored in a memory of the sensor module. After the calibration, the sensor module again is separated from the calibration device and can be inserted into its actual analysis device or measuring system.

The calibration system is not limited to the calibration of a particular type of sensor, but can be used for a plurality of different sensors. It is possible to store calibration data for different sensor modules in the control unit of the calibration device, so that after identification of the sensor module the calibration device can fall back on the stored data for carrying out the calibration process.

Preferably, the calibration data specific for the respective sensor module including at least one specific calibration cycle (preferably several calibration cycles), which defines its calibration, are stored however in the sensor module itself, e.g. in an electronic unit of the sensor module, and are read out by the calibration device for the calibration process. This has the advantage that in the calibration system it is also possible to calibrate newly developed sensor modules whose data are not stored in the controller of the calibration device, without first carrying out an update of the calibration device. The calibration cycle as well as other calibration data specific for the respective sensor module can be stored in a read-only memory of the sensor module, which in particular is part of the electronic unit preferably including one or more microchips. The electronic unit is an integral part of the sensor module.

The calibration data in particular include data which provide for the identification of particular types of sensor and the associated sensor modules, e.g. type designations, serial numbers and other manufacturer information.

Such data for the identification of various sensor modules to be connected preferably are stored in the sensor module, but can also be stored in the controller.

In the controller, there can also be stored various calibration cycles which are associated to different types of sensor or types of sensor modules. Here, these data also are counted among the calibration data.

Since the data specific for the respective sensor module are stored either in the sensor module itself or in the calibration device, each type of sensor can be treated with its own calibration cycle, which in particular can differ in the type, the sequence and/or the quantity of the calibration fluids supplied to the sensor and possibly preceding, succeeding and/or interposed rinsing operations. After going through a calibration cycle, the calibration of the sensor in the sensor module is terminated.

When the specific data are stored in the sensor module itself, sensor modules developed later on also can be used and calibrated in the calibration system, because the specific data or the "intelligence" so to speak is/are included in the sensor module.

To increase the user friendliness, identification data and possibly calibration data of a connected sensor module advantageously are collected automatically by the calibration device on connection of a sensor module via the interface. It is conceivable, however, to also provide for a manual input of the identification data of a sensor module.

The controller preferably is programmed such that after connection of a sensor module to the interface it initiates an identification cycle to identify the type of sensor of the connected sensor module. For example, on plug-in of a sensor module it can be monitored by the controller which sensor logs in to a bus system of the calibration device. Advantageously, there are transmitted data which provide for the identification of the sensor as well as calibration data of the sensor module. Alternatively, matching with a list of sensor data stored in the controller can also be effected, wherein the controller then selects the exactly fitting calibration cycle with the appropriate calibration steps for this type of sensor.

When calibrating the sensors, several calibration fluids can be used. For this purpose, the calibration device for example includes a plurality of calibration fluid receptacles for inserting calibration fluid containers with various calibration fluids.

For each calibration fluid a separate calibration fluid container can be inserted. Alternatively, or in addition, however, cartridges also can be used as calibration fluid containers, in each of which several calibration fluid containers with possibly different calibration fluids are combined, which are replaced as a whole, wherein the cartridge is insertable into a calibration fluid receptacle. It is of course also possible to provide cartridges with different sets of calibration fluids for different types of sensor.

As one of the calibration fluids a generally usable rinsing or cleaning fluid can be provided. This rinsing or cleaning fluid can be provided in a separate container with mostly larger capacity, which for example is placed in an especially provided calibration fluid receptacle. A calibration fluid container with rinsing or cleaning fluid however also can be part of a cartridge as described above.

To simplify an exchange of the calibration fluid containers, the calibration fluid receptacles preferably have fluidic interfaces which are formed such that the calibration fluid containers can be inserted and be removed again without using a tool. The interfaces form a passage which is fluid-tight with respect to the environment from the inserted calibration fluid container to the fluid lines of the calibration device.

In addition, a separate calibration fluid container preferably is provided, which serves as waste collection container for receiving the used calibration, rinsing and cleaning fluids.

The identification of the inserted calibration fluid containers also can be automated, for example, in the region of the at least one calibration fluid receptacle an identification sensor for identifying the inserted calibration fluid container can be present, wherein the identification sensor is coupled with the controller. In this way, on insertion of a new individual calibration fluid container or a new cartridge with several calibration fluids matching can be effected directly via the controller as to whether the calibration fluid or the cartridge is suitable for this system and includes the correct calibration fluids for the currently connected sensor module. This also allows one to insert the calibration fluid containers in an arbitrary arrangement into the calibration fluid receptacles, without a receptacle having to be associated to a particular calibration fluid.

For identifying the respective calibration fluid or respective cartridge a bar code or an EEPROM can be present at the at least one calibration fluid container or the cartridge, wherein the identification sensor then is part of a bar code reader or an EEPROM reading device.

The connected sensor module to be calibrated for example has optical and/or electrochemical sensors which are calibrated in the calibration device.

Possible types of sensors that can be contained in a sensor module include, for example, sensors for determining the pH value, the turbidity, the electrical conductivity, the oxidation and/or reduction potential, the spectral absorption coefficient of a fluid or also a concentration of chlorine or of chlorine dioxide in the fluid. Arbitrary combinations of sensors can also be provided, which, for example, can be calibrated one after the other. In the sensor modules, further sensors not mentioned here can of course also be provided, which then can be calibrated with suitable calibration fluids and suitable calibration cycles.

Preferably, the sensor module can be coupled to the electric and to the fluidic interface at the same time by a plug connection, so that the sensor module can be connected with the calibration device by plug-in only, without having to connect or release hose connections or without having to individually close or release electric cable connections.

The calibration fluid preferably is moved through the sensor module by a pump arranged in the calibration device downstream of the interface. This arrangement in particular provides for using an inexpensive diaphragm pump as pump, even if in operation the same possibly should produce microscopic air bubbles. Such air bubbles would negatively influence a calibration, for example, of a turbidity sensor, but in the case of a downstream arrangement of the pump the air bubbles cannot get from the calibration device into the sensor and therefore cannot influence the measurement.

On its downstream side, the pump advantageously is connected with a calibration fluid container serving as waste collection container, which takes up the fluids delivered by the pump.

On the waste collection container, a weight sensor can be arranged, via which a total flow of calibration fluids through the sensor module and the calibration device is detected. By means of the weight sensor it can also be monitored whether calibration fluid or rinsing solution containers are empty, as in this case no fluid is moved through the system and correspondingly there is no increase in weight of the waste collection container.

The pump for pumping the calibration fluids can be mounted on the housing of the calibration device such that vibrations generated by the pump are transmitted to the sensor module. Gas bubbles possibly present in the sensor module can be released by the vibrations, so that the same can be moved out of the sensor module with the fluid stream. This is recommended in particular when a rinsing step with a rinsing or cleaning fluid is effected before the actual calibration. In the succeeding calibration with the actual calibration solution(s), the sensor then is free from gas bubbles, and the quality of the calibration increases.

To cause this effect, the pump, for example, can be mounted on that part of the outer housing of the calibration device on which the interface for the sensor module is seated as well.

The interface for the sensor module can be formed e.g. in the form of a sensor connecting plate in which the fluid ports for the fluidic interface are formed and in which a plug also is provided as electric interface. The fluid ports permanently are connected with fluid lines in the interior of the calibration device, while the plug permanently is electrically connected with the controller via an electric supply line and a data line. The interface of course also can be formed in some other way.

Between the plurality of calibration fluid receptacles and the interface switchable valves preferably are provided, which open and/or close an inflow channel of the respective calibration fluid interface. In this way, each calibration fluid container can be actuated individually, and each calibration fluid individually can be supplied to the sensor module in an arbitrary order and duration specified by the controller within the calibration cycle for the respective sensor. Likewise, a rinsing or cleaning fluid or also air for example can selectively be supplied individually or possibly be admixed to a calibration fluid.

For the duration of the calibration, the fluid ports of the sensor module remain continuously connected with the fluidic interface. Switching valves can of course be provided. However, the sensor module remains continuously coupled to the calibration device until the calibration process is completed.

In general, the calibration device preferably includes a plurality of calibration fluid receptacles for different calibration fluids, so that a plurality of different sensor modules to be coupled to the interface can be provided in the calibration system.

The system in which the sensor modules for detecting specific measurement values are inserted, for example, can be a water analysis device with which drinking water for instance is monitored.

The calibration system according to the invention can be operated as an additional system for such an analysis device, wherein the sensors inserted in the water analysis device are removed from the water analysis device, via the interfaces are connected with the calibration device of the calibration system, are calibrated there, are again separated from the calibration device and subsequently are again inserted into the water analysis device. It is of course also possible to first calibrate new sensors for the water analysis device in the calibration system and subsequently insert the calibrated sensors into the water analysis device.

The calibration system, however, can of course also be used for analysis devices for other fluids apart from water. The calibration system according to the invention in principle is usable both for sensors to be newly installed and for sensors to be recalibrated.

By using an independent calibration system separate from the actual analysis system with its own calibration device the fluid paths can be kept very short, which allows an economical use of the calibration fluids. In addition, aggressive fluids also can be used for calibrating, which possibly might impair other parts of the actual analysis device. In this way, a more exact calibration is possible. In addition, an individual sensor each can selectively and separately be calibrated in the calibration system, when the different sensors of the actual analysis device are contained in different sensor modules. In this way, an impairment of the other sensors of the analysis device is safely prevented, because the individual sensor modules are calibrated separately.

By an automatic recognition of the respective sensor module coupled to the calibration device and connected with the same via the interfaces, the operating expenditure for the user can be reduced to a minimum. The same applies for the use of the correct calibration fluids, which via the inserted calibration fluid containers and the automatic recognition of the respectively inserted calibration fluid containers can be used correctly and require only little user interaction.

BRIEF DESCRIPTION OF THE DRAWINGS

FIG. 3 shows the calibration device of FIG. 2 with a sensor module plugged in.

DETAILED DESCRIPTION

Figure 1:
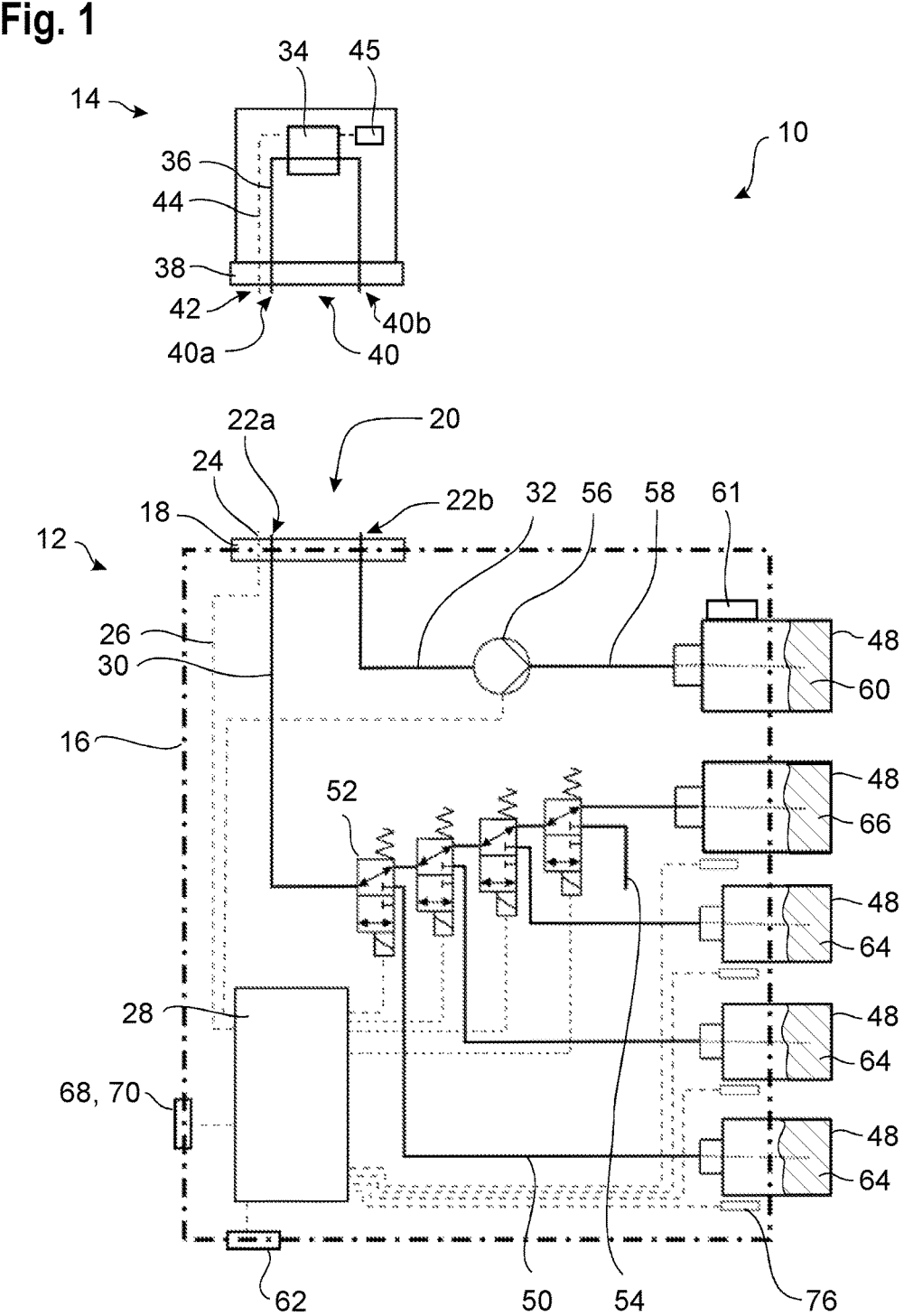
FIG. 1 shows a schematic overview drawing of a calibration system according to the invention.

FIG. 1 shows a calibration system 10 which comprises a calibration device 12 and at least one sensor module 14 to be calibrated, which is releasably connectable therewith. The sensor module 14 is a unit constructionally separate from the calibration device 12.

The calibration device 12 is an independent appliance which includes an enclosing outer housing 16. In the outer housing 16 a sensor connecting plate 18 is inserted, which has an interface 20 for connection of the sensor module 14. The interface 20 can of course also be realized in a way other than in the form of the illustrated sensor connecting plate 18.

The interface 20 comprises a fluidic interface 22a, 22b which comprises two fluid ports leading into the interior of the outer housing 16 of the calibration device 12, which form a fluid feed line and a fluid discharge line and which are connected with fluid feed and discharge lines 30, 32 in the interior of the calibration device 12.

In addition, the interface 20 comprises an electric interface 24 into which one or more power and/or data lines 26 open, for example, in a plug. The power and/or data lines 26 are connected with a controller 28 of the calibration device 12, which likewise is arranged in the interior of the outer housing 16.

The fluidic interface 22a, 22b and the electric interface 24 are arranged in direct vicinity to each other. The interface 20 is formed such that both the fluidic ports and the electric ports can be connected with a single plug-in operation of the sensor module 14.

When no sensor module 14 is attached, the fluidic interfaces 22a, 22b here are closed fluid-tight, in order to prevent a leakage of fluid from the calibration device 12. Clearing and closing the fluidic interfaces 22a, 22b is effected automatically via a suitable, non-illustrated mechanism.

The sensor module 14 includes one or more sensors 34 which can detect measurement data from a fluid. The fluid to be measured is supplied to the sensor 34 through a fluid line 36 extending in the sensor module 14, which opens into an interface 38. The interface 38 here is formed as connecting plate and generally includes two fluid ports 40a, 40b and in addition an electric port 42. The electric port 42 is connected with an electric power and/or data line 44 in the interior of the sensor module 14, which leads to the sensor 34 and an electronic unit 45 connected with the sensor 34, which in particular includes one or more microchips. The electronic unit 45 here comprises a read-only memory in which specific calibration data such as e.g. identity data and a calibration cycle for the respective sensor module 14 are stored.

The fluid ports 40a, 40b are formed and arranged such that when plugging the interface 38 of the sensor module 14 onto the interface 20 at the outer housing 16 of the calibration device 12, the fluid ports 22a and 40a as well as the fluid ports 22b and 40b adjoin each other. Thus, by simply plugging the sensor module 14 onto the interface 20 of the calibration device 12 a connection fluid-tight to the outside is obtained, via which the fluid feed and discharge lines 30, 32 of the calibration device 12 continuously are fluidically connected with the fluid line 36 in the interior of the sensor module 14 for the duration of the calibration process.

At the same time, the electric port 42 of the sensor module 14 is brought into electrical contact with the electric interface 24 of the interface 20 of the calibration device 12. For this purpose, a plug can be formed at the interface 38, which on attachment of the sensor module 14 gets in engagement with the electric interface 24 compatible with this plug.

Figure 2:
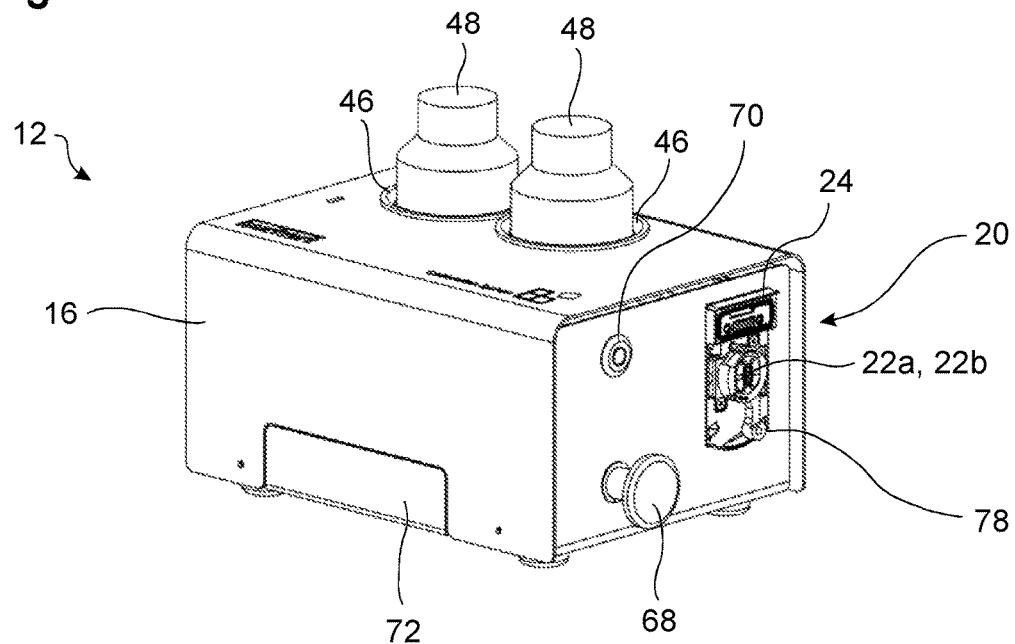
FIG. 2 shows a calibration device of the calibration system according to the invention as shown in FIG. 1.
Figure 3:
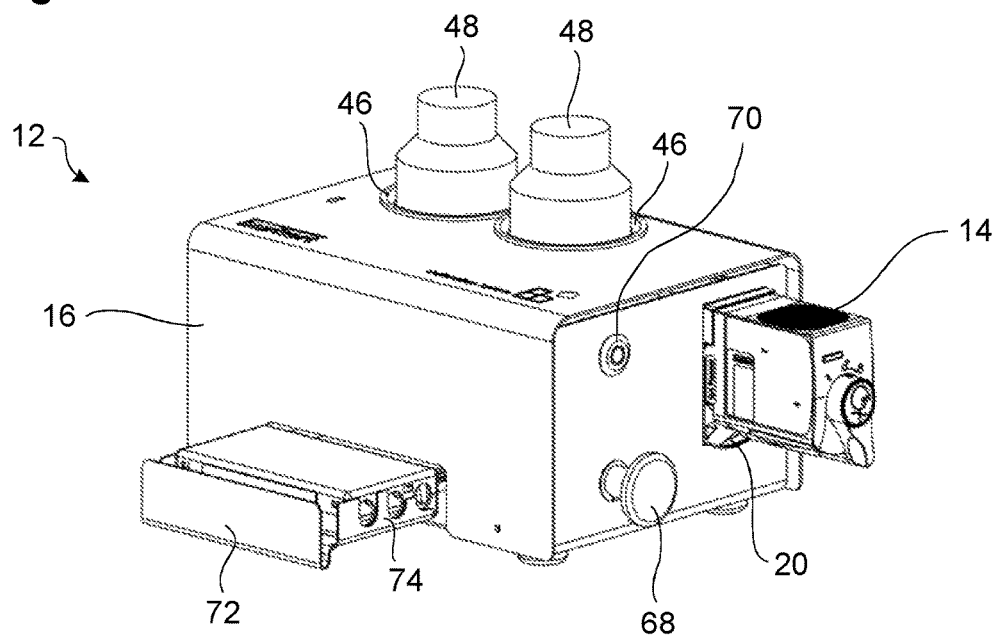

The calibration device 12 includes a plurality of calibration fluid receptacles 46 which are accessible from the outside of the outer housing 16 and into each of which a calibration fluid container 48 can be inserted (see also FIGS. 2 and 3).

The calibration fluid containers 48 are connected with the fluid feed line 30 via inflow channels 50 and cascadingly switched valves 52. Each of the valves 52 can be actuated individually by the controller 28, so that the fluid contained in the respective calibration fluid container 48 selectively can be delivered to the fluid port 22a and thus into the sensor module 14 for a particular duration and in a particular quantity. An arbitrary mixture of the respective calibration fluids also is possible.

In FIG. 1, not all of the identical components each are provided with reference numerals for reasons of clarity.

To one of the valves 52, here the one located farthest upstream, an air supply 54 additionally is connected, through which ambient air can be fed into the fluid feed line 30.

In the fluid discharge line a pump 56 is arranged downstream of the sensor module 14, which effects the movement of the fluids through the fluid line 36 of the sensor module 14. The pump 56 is connected with the controller 28 via an electric line and is supplied with current by said controller and receives the necessary actuation signals from the same.

Downstream of the pump 56 a fluid line 58 is provided, which opens into one of the calibration fluid receptacles 46 and thus leads to one of the calibration fluid containers 48. This calibration fluid container 48 serves as waste collection container in which the entire fluid 60 flushed through the sensor module 14 is collected, in order to be disposed of later on.

At the waste collection container, a weight sensor 61 is provided here, which detects the total weight of the waste collection container. The controller 28 is designed such that via the weight sensor 61 a total flow of fluids through the sensor module 14 and the calibration device 12 also is detected. Beside possible monitoring of the filling level of the waste collection container, it thus can also be checked whether fluid at all is pumped out of the individual calibration fluid containers 48 or out of a rinsing fluid container. For example, it can thus be detected when a calibration fluid container 48 or a rinsing fluid container is empty.

The calibration device 12 can be operated individually and autarkically, but in this example an electronic interface 62 is provided, via which the controller 28 can be connected with further (non-illustrated) electronic devices or for example with a network and/or a control PC. Via the interface 62 the electric power supply of the calibration device 12 can also be effected, e.g. via an external power supply unit or a connected suitable data bus. Alternatively, an integrated accumulator also can be provided for energy supply.

The calibration system 10 serves to calibrate the one or more sensors 34 of the sensor module 14. For this purpose, the sensor module 14 is plugged onto the interface 20 of the calibration device 12, so that the electric port 42 of the sensor module 14 is connected with the electric interface 24 of the calibration device 12 and the fluid line 36 is fluidically connected with the fluid feed and discharge lines 30, 32 via the fluidic interface 22a, 22b.

Subsequently a calibration process is started, in which one or more calibration fluids 64 are passed from the calibration fluid containers 48 to the sensor 34 and from there flow off into the calibration fluid container 48 serving as waste collection container. The sensor 34 communicates the respectively detected measurement values to the controller 28 of the calibration device 12, where they are evaluated. Due to the determined measurement values of the sensor 34, the controller 28 performs a calibration with the aid of the standardized calibration fluids 64 in the calibration fluid containers 48. The received data for the calibration of the sensor 34 of this specific sensor module 14 are stored in the sensor module 14. The sensor module 14 thus is calibrated completely and can again be released from the calibration device 12 and be inserted in its actual measurement system.

The procedure can then be continued with further sensor modules 14. The sensors 34 of the individual sensor modules 14 can differ from each other in terms of type, construction and measurement behavior. Among other things, optical and/or electrochemical sensors 34 can be provided, which each are calibrated with the calibration device 12.

For example, sensors 34 can be provided in different sensor modules 14, which allow a determination of a pH value of a fluid, of the turbidity, the electrical conductivity, the oxidation and/or reduction potential, the spectral absorption coefficient, and a concentration of chlorine and/or chlorine dioxide in the fluid. In particular, sensor modules 14 which are used for water analysis devices, for example for the analysis of drinking water, can be calibrated in the calibration device 12.

In the variant shown here, the controller 28 automatically recognizes the type of sensor module 14 coupled thereto and of the sensor 34 contained therein.

When plugging the sensor module 14 onto the interface 20 of the calibration device 12, the controller 28 then electrically connected with the sensor 34 for this purpose receives the data automatically output by the sensor 34 on connection with a voltage source, which data allow an unambiguous identification of the type of sensor 34. In addition, the calibration data stored in the sensor module are transmitted to the controller 28 of the calibration device 12.

Due to this so-called hot-plug functionality, an action of the user to identify the sensor 34 is not required. To achieve this functionality, the power and data line 26 as well as the power and data line 44 in this example are formed as CAN bus, wherein in addition an especially adapted protocol based on CANopen is used, which allows the hot-plug functionality.

Alternatively, the identity data received are compared with the stored calibration data in the controller 28. After the controller 28 has identified the exact type of the sensor 34, it selects a suitable calibration cycle from among the calibration data stored in it.

In both cases, the controller 28 actuates the valves 52 and the pump 56 corresponding to the specific calibration cycle, wherein one or more calibration fluids 64 are supplied from the calibration fluid containers 48 to the sensor 34. By clearly recognizing and identifying the sensor 34 it is ensured that always the correct calibration cycle is performed. The calibration fluids 64 each have particular known properties, such as different pH values, different known turbidities or the like.

In the embodiment shown here, one of the calibration fluid containers 48 does not contain a calibration fluid 64 in the actual sense, but a rinsing or cleaning fluid 66, for example water. At the beginning and at the end, but also between the individual calibration steps carried out with different calibration fluids 64 this rinsing or cleaning fluid 66 can be used for rinsing the sensor 34 and the fluid lines 30, 36, 32.

With the calibration system 10 it also is possible to merely carry out cleaning of a sensor module 14 and in doing so refrain from a recalibration.

In the simplest case, a calibration cycle automatically starts with plugging the sensor module 14 onto the interface 20. When the sensor module 14 is plugged in, the controller 28 communicates with the sensor module 14 and determines the type of sensor 34 contained in the sensor module 14 and then automatically performs the suitable calibration cycle.

Alternatively, a calibration cycle can be initiated by actuating an input element 68 at the outer housing 16 of the calibration device 12, which e.g. is implemented as simple pushbutton. When a user presses the pushbutton an input signal is generated, which causes the controller 28 to start the correct calibration cycle.

Beside the simple actuation of the input element 68, a calibration cycle also can be effected via a connected USB-CAN dongle. Via a computer with a corresponding software, the calibration process thus can be carried out with a larger number of adjustable parameters. When the controller 28 is connected with other appliances or a network via the interface 62, the calibration process for example also can be controlled via another appliance in a complex bus system. It just as well is possible to graphically display the exact sequence of the respective calibration cycle on another appliance.

The calibration can be carried out as single-point calibration or as multi-point calibration, for example up to a four-point calibration. For each calibration point, which corresponds to a step of flushing the sensor 34 with a particular calibration fluid 64 in the corresponding calibration cycle, a separate calibration fluid 64 preferably is used. The respective measurement value of the sensor 34 is ascribed to the corresponding value of the respective calibration fluid 64 and stored.

It also is possible to carry out a quality control in that e.g. in a two-point calibration a third calibration point is detected and it is checked whether this third calibration point lies on the straight line defined by the two-point calibration. Only when the quality control is successful, the new calibration is written into the read-only memory of the electronics 45 of the sensor unit 14.

A display device 70, for example in the form of a multicolored LED, each provides the user with information on the calibration process taking place. Instead of a single colored LED, the display 70 of course can also be formed e.g. in the form of a display screen for outputting text or the like.

It also is possible to only connect a display screen via a CAN bus when needed and otherwise output information only via a status LED.

Since the pump 56 is arranged downstream of the sensor 34, the calibration fluids 64 and the rinsing or cleaning fluid 66 are sucked through the sensor 34. In this way, it is avoided that possible air bubbles produced in the pump 56 get into the sensor 34.

The vibrations produced by the pump 56 can be used for example to support cleaning of the sensor 34 or of the fluid line 36 of the sensor module 14. For this purpose, the pump 56 here is mounted on that part of the outer housing 16 on which the interface 20, i.e. in this case the sensor connecting plate 18, also is seated. Thus, the vibrations of the pump 56 are transmitted to the sensor module 14 and help to expel contaminations or gas bubbles from the fluid lines 36 of the sensor module 14.

This is particularly effective when the sensor 34 contains one or more glass capillaries, in order to release air bubbles from the glass capillary. This is advantageous for example when the sensor 34 is a turbidity sensor, as air bubbles in the measurement chamber would distort the measurement result or calibration result. In principle, this applies for all optical measurement methods.

For cleaning and/or for preparing the sensor module 14 for the calibration, the introduction of air also can be employed. Above all in the case of optical sensors, in which possible gas bubbles in the measurement chamber would distort the measurement result, the measurement system of the sensor module 14 for example first can completely be filled with air and subsequently slowly be filled with the rinsing or cleaning fluid 66. With this method, the remaining air bubbles are removed from the sensor 34. Subsequently, the sensor 34 is ready for the calibration with one or more calibration fluids 64.

Figure 4:
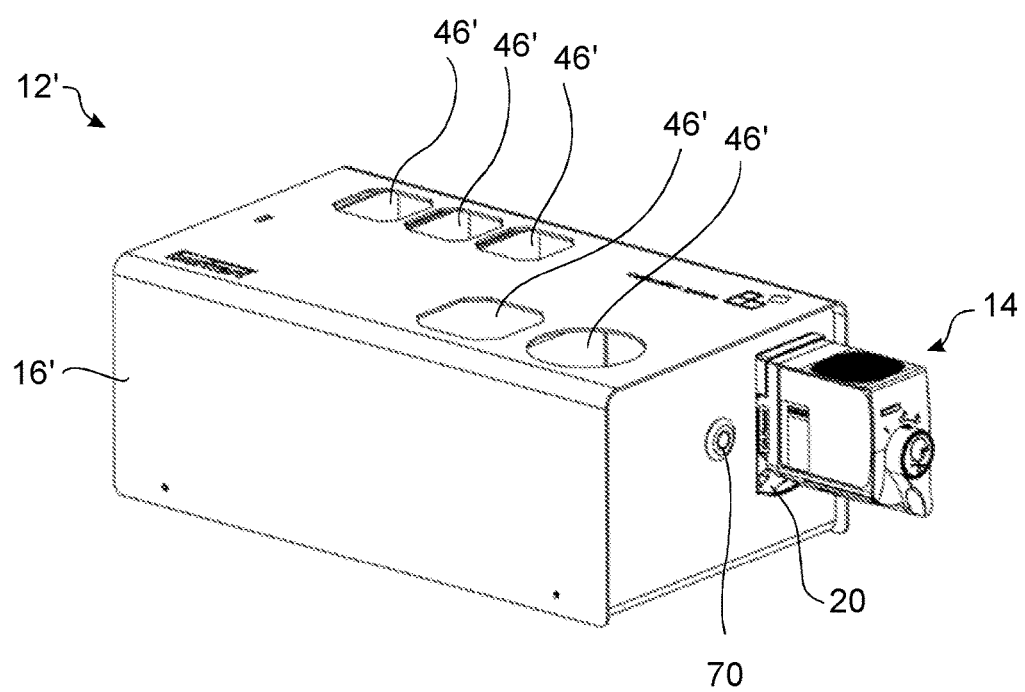
FIG. 4 shows a variant of the calibration device represented in FIG. 2.

The calibration fluid containers 48 each can be inserted into a separate calibration fluid receptacle 46, as this is shown in FIGS. 2 to 4.

The calibration fluid receptacles 46 each have a non-illustrated fluid interface, via which a fluid connection to the inflow channels 50 exists. These fluid interfaces are formed such that the calibration fluid containers 48 easily can be plugged into the calibration fluid receptacles 46 without use of a tool and can be pulled out of the same, in order to exchange the calibration fluid container 48.

FIG. 4 shows a variant in which the calibration fluid receptacles 46' in the outer housing 16' of the calibration device 12' are coded in their shape, so that calibration fluid containers which contain special calibration fluids can only be inserted into particular receptacles, while one receptacle each is provided for a (larger) bottle of a rinsing or cleaning fluid or of a waste collection container.

Alternatively, or in addition, in both variants shown a receiving drawer 72 is provided as calibration fluid receptacle, into which a non-illustrated cartridge 74 can be inserted as calibration fluid container, which contains one or more calibration fluids. The cartridge 74 can be designed refillable, or be formed as disposable article.

To each of the calibration fluid receptacles 46, 46' a reading device with an identification sensor 76 (see FIG. 1) here is associated, which detects the identity of a calibration fluid container 48 or a cartridge 74 with calibration fluids plugged in. For this purpose, a bar code can be imprinted for example on the respective calibration fluid container 48 or on the respective cartridge 74 with calibration fluids, and the reading device is a bar code reader. The collected data are communicated to the controller 28 and evaluated in the same. In another embodiment, the reading device is an EEPROM reader and each calibration fluid container 48 or cartridge 74 with calibration fluids plugged in has its own EEPROM in which the respective data essential for the identification of the calibration fluids contained are stored. This EEPROM is read out by the reading device, and the data are communicated to the controller 28. In this way, a calibration fluid container 48 can be inserted into any appropriate calibration fluid receptacle 46, 46', as the calibration device 12 performs a clear allocation after insertion of the calibration fluid container 48.

The controller 28 evaluates the data transmitted by the reading device and checks whether the calibration fluid containers 48 presently contained in the calibration fluid receptacles 46 with the calibration fluids contained therein fit with the calibration cycle selected for the sensor module 14 coupled to the interface 20 and the sensor 34 contained therein. If this is not the case, an error message is issued, for example via the display 70 in the form of a red light.

In this example, a fastening element 78 is provided at the interface 20, which in the coupled condition safely holds the sensor module 14 at the calibration device 12. In this example, the fastening element 78 is a mechanical snap-in lever.

The invention claimed:

1. A calibration system with a calibration device which includes an electric and fluidic interface for releasably connecting at least one sensor module to be calibrated, which sensor module is a unit constructionally separate from the calibration device and contains one or more sensors, at least one calibration fluid receptacle into which a calibration fluid container containing a calibration fluid is inserted, an identification sensor to detect the identity of the calibration fluid container so as to determine whether the calibration fluid in the calibration fluid container is correct for calibrating a connected sensor module, and a controller to which the identification sensor is coupled, which controller controls the flow of calibration fluid through the sensor module connected to the calibration device and which is electrically coupled with the connected sensor module via the electric interface and can collect measurement data from the sensor module, wherein in the calibration system calibration data are stored, so that the calibration device can calibrate various sensor modules which are coupled to the interface.

2. The calibration system according to claim 1, characterized in that the calibration data for the sensor module are stored in the sensor module or an electronic unit of the sensor module.

3. The calibration system according to claim 1, characterized in that in the sensor module at least one calibration cycle is stored for the sensor module.

4. The calibration system according to claim 3, characterized in that the controller is programmed such that after connection of a sensor module to the interface the controller initiates an identification cycle for identifying the type of sensor of the sensor module.

5. The calibration system according to claim 1, characterized in that the calibration device has several calibration fluid receptacles for inserting calibration fluid containers with various calibration fluids.

6. The calibration system according to claim 5, characterized in that the calibration fluid receptacles have fluidic interfaces which are formed such that the calibration fluid containers can be inserted and be removed again without use of a tool.

7. The calibration system according to claim 1, characterized in that on at least one calibration fluid container a bar code or an EEPROM is present and the identification sensor is part of a bar code reader or an EEPROM reading device.

8. The calibration system according to claim 1, characterized in that the at least one sensor module has optical and/or electrochemical sensors which are calibrated.

9. The calibration system according to claim 1, characterized in that the at least one sensor module is provided with a sensor for determining a pH value, turbidity, electrical conductivity, oxidation potential, reduction potential and/or spectral absorption coefficient of a fluid, and/or concentration of chlorine and/or chlorine dioxide in the fluid.

10. The calibration system according to claim 1, characterized in that the sensor module can be coupled by a plug connection to the electric and the fluidic interface at the same time.

11. The calibration system according to claim 1, characterized in that the calibration device is provided with a pump for pumping the calibration fluid, which pump is arranged downstream of the interface.

12. The calibration system according to claim 1, characterized in that the calibration device includes a pump for pumping calibration fluid, which is mounted on a housing of the calibration device such that vibrations generated by the pump are transmitted to the sensor module.

13. The calibration system according to claim 12, characterized in that the pump is mounted on a part of the housing of the calibration device on which the interface also is seated.

14. The calibration system according to claim 1, characterized in that the calibration fluid container is formed as cartridge which contains several calibration fluids.

15. A calibration system with a calibration device which includes an electric and fluidic interface for releasably connecting at least one sensor module to be calibrated, which sensor module is a unit constructionally separate from the calibration device and contains one or more sensors, a plurality of calibration fluid receptacles into which calibration fluid containers containing different calibration fluids are inserted, identification sensors to detect the identity of each calibration fluid container so as to determine whether the calibration fluids in the calibration fluid containers are correct for calibrating a connected sensor module, and a controller to which the identification sensors are coupled, which controller controls the flow of calibration fluid through the sensor module connected to the calibration device and which is electrically coupled with the connected sensor module via the electric interface and can collect measurement data from the sensor module, wherein in the calibration system calibration data are stored, so that the calibration device can calibrate various sensor modules which are coupled to the interface.

16. The calibration system according to claim 15, characterized in that between the plurality of calibration fluid receptacles and the interface, switchable valves are provided, which open or close an inflow channel of the respective calibration fluid to the interface.

\* \* \* \* \*